United States Patent [19]

Nunokawa

[11] Patent Number: 4,838,680
[45] Date of Patent: Jun. 13, 1989

[54] OPTICAL SYSTEM FOR RETINAL CAMERA

[75] Inventor: Kazuo Nunokawa, Tokyo, Japan

[73] Assignee: Tokyo Kogaku Kikai Kabushiki Kaisha, Tokyo, Japan

[21] Appl. No.: 161,221

[22] Filed: Feb. 17, 1988

[30] Foreign Application Priority Data

May 30, 1984 [JP] Japan .................. 59-109896

[51] Int. Cl.⁴ .............................. A61B 3/14
[52] U.S. Cl. ....................... 351/206; 354/62
[58] Field of Search .............. 351/205, 206, 221; 354/62

[56] References Cited

U.S. PATENT DOCUMENTS 4,322,137  3/1982  Nohda ................. 351/206

Primary Examiner—Rodney B. Bovernick
Assistant Examiner—P. M. Dzierzynski
Attorney, Agent, or Firm—Brumbaugh, Graves, Donohue & Raymond

[57] ABSTRACT

An optical system for a retinal camera comprises objective lens adapted to be located toward a patient's eye. The retina of the patient's eye is illuminated and photographed through the objective lens, which has a first biconvex type lens means and a second biconvex type lens means with a space between them, the first biconvex type lens means has a curvature radius of the first convex surface open to the air and faces toward the eye of which is larger than that of the other second convex surfaces open to the air, and the second biconvex type lens means of which curvature radius of third convex surface open to the air and facing toward the first biconvex type lens means is larger than that of the other fourth convex surfaces open to the air.

6 Claims, 4 Drawing Sheets

OPTICAL SYSTEM FOR RETINAL CAMERA

This application is a continuation of application Ser. No. 736,560, filed on May 21, 1985 now abandoned.

BACKGROUND OF THE INVENTION

1. Field of the Invention

The present invention relates to an optical system for a retinal camera, and more particularly to an optical system for a retinal camera having a wide viewing angle and which does not generate flares or ghosts in pictures taken by the camera.

2. Description of Prior Art

In a retinal camera, it is desirable that the objective lens has a wide view field so that it can take a picture of a wide range of the eye fundus. Conventional optical systems for retinal cameras are generally designed so that the eye fundus is illuminated through the objective lens. With such an arrangement, however, the illuminating beam is reflected by each surface of the objective lens, generating flares or ghosts, so that the quality of the picture is lowered.

For such reason, there are provided black points or images of black points covering the area of passage of the illuminating beam at the predetermined surfaces of the objective lens, and said images of the black points are produced by black points provided conjugate with the predetermined surfaces of the objective lens with respect to relay lenses, so that harmful beams are prevented from being mixed in with the photography beam.

In conventional retinal cameras, among objective lenses there are known those comprised of a small number of lenses, for example, positive meniscus lens, a biconvex lens, and a combination of meniscus lens and a biconvex lens. However, the positive meniscus lens cannot be designed with a viewing angle greater than 30°. The biconvex lens can have a viewing angle of about 50°, but it is difficult to correct various aberations. The combination of a meniscus lens and a biconvex lens cannot be designed so as to have a long working distance, meaning the spacing between the patient's eye and the objective lens.

To overcome the disadvantages of these lenses, the number of the lenses must be increased. If the number of the lenses is increased, the number of black points for preventing the harmful beam from mixing with the photographing beam must be increased, so that the illuminating beam or the photographing beam is decreased.

DESCRIPTION OF THE INVENTION

Object of the Invention

It is an object of the present invention to provide an optical system for a retinal camera which does not generate flares or ghosts, and which has a small number of lenses and a long working distance.

Another object of the present invention is to provide an optical system for a retinal camera having an objective lens the various aberrations of which can be readily corrected.

Summary of the Invention

According to the present invention, the above and other objects can be accomplished by an optical system for a retinal camera including objective lens means adapted to be placed opposite to a patient's eye with an air space therebetween, illumination optical system for projecting beams of illumination light through said objective lens means to said patient's eye, photographing optical system for observing retina of said patient's eye through said objective lens means, said objective lens means including first biconvex type lens means closer to said patient's eye and second biconvex type lens means further to said patient's eye, said first biconvex type lens means having a curvature radius of the first convex surface open to the air and facing toward the eye of which is larger than that of the other second convex surface open to the air, said second biconvex type lens means of which curvature radius of third convex surface open to the air and facing toward the first biconvex type lens means is larger than that of the other fourth convex surface open to the air, and further comprising an optical path dividing means being provided on the opposite side of the objective lens means from that of the eye for dividing the optical path passing through the objective lens means into two sub-optical paths, a photographing optical system being located on one of the sub-optical paths, and an illuminating optical system and harmful beam blocking means being located on the other thereof.

In a preferable aspect of the present invention, the second and fourth convex surfaces are of nonspherical configurations.

In another aspect of the present invention, the photographing optical system has a beam restriction means and the first and fourth convex surfaces are designed so that images of the beam restriction means reflecting thereby are formed at the same position where the harmful beam blocking means is provided.

In another aspect of the present invention, the center of the curvature of the third convex surface is conjugate with the beam restriction means with respect to the second biconvex type lens means.

According to another aspect of the present invention, the second biconvex type lens means consists of a biconvex lens and a meniscus lens which are joined to each other.

According to another aspect of the present invention, the photographing optical system has a beam restriction means, and the first and fourth convex surfaces and the joined surface of the second biconvex type lens means are designed so that images of the beam restriction means reflected at these surfaces are formed at the same position where the harmful beam blocking means is provided.

In further preferable aspect of the present invention, the center of the curvature of the third convex surface is conjugate with the beam restriction means with respect to the second biconvex type lens means.

The above and other objects and features of the present invention will become apparent from the following description of a preferred embodiment with reference to the accompanying drawings.

DESCRIPTION OF THE PREFERRED EMBODIMENT

Figure 1:
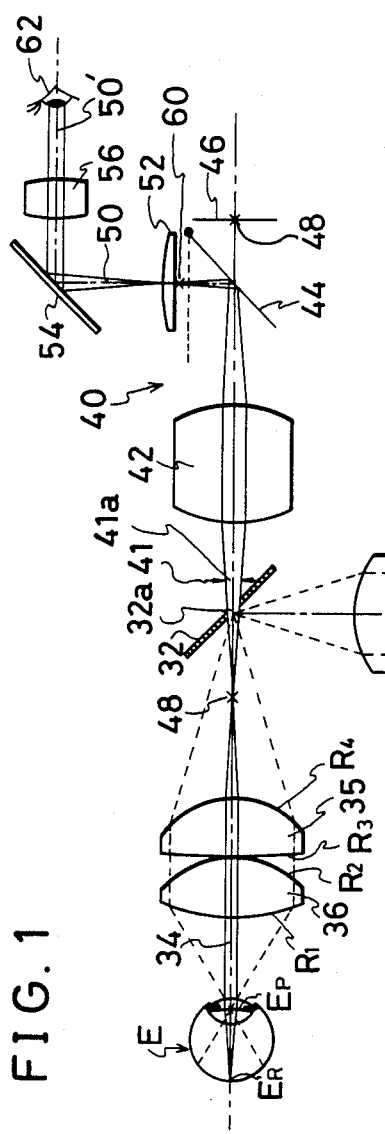
FIG. 1 is a diagrammatic illustration of the optical system for a retinal camera in accordance with one embodiment of the present invention.

Referring to the drawings, there is shown an optical system for a retinal camera which includes an illuminating optical system and a photographing and observing optical system.

FIG. 1 shows the optical system for a retinal camera which comprises an illuminating optical system 10 for illuminating the retina $E_R$ of a patient's eye E and a photographing and observing optical system 40 for observing and taking pictures of the retina $E_R$.

The illuminating optical system 10 has a xenon photographic light source 14 located on an illuminating optical axis 13 and a tungsten-filament observation lamp 12 provided on the optical axis of a beam reflected at an oblique half mirror 18. There is provided a first condenser lens 16 between the half mirror 18 and the lamp 12, and a second condenser lens 22 between the half mirror 18 and the light source 14.

Figure 2:
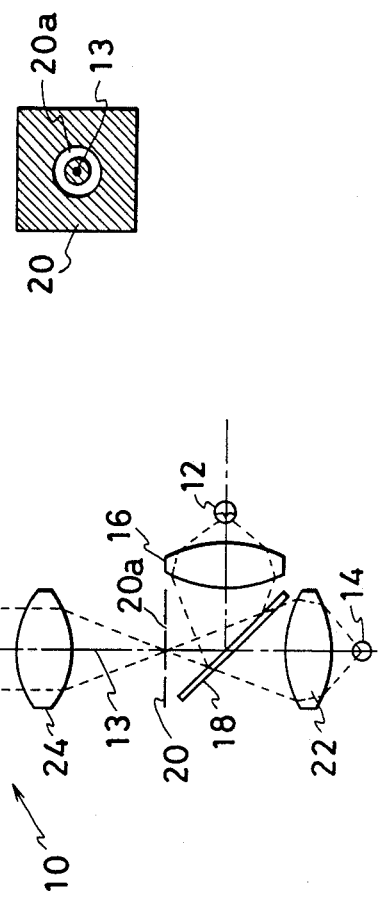
FIG. 2 is a plan view of a ring slit.

On the optical axis 13 there is provided a ring slit plate 20 located conjugate with the lamp 12 and the light source 14 with respect to the condenser lenses 16 and 22, respectively. The ring slit plate 20, as shown in FIG. 2, has a ring slit 20a centered on the axis 13 to generate a second ring-shaped light source.

The illuminating optical system 10 further includes a first relay lens 24, a first black point plate 26 having a first black point 26', a second black point plate 28 having a second black point 28', a second relay lens 30, and an obliquely disposed mirror 32 having an aperture 32a at the center thereof, which are arranged in this order along the axis 13 from the ring slit plate 20. The first relay lens 24 is located so as to focus on the ring slit plate 20, and the second relay lens 30 is located so as to focus on the aperture 32a, so the illumination beam of light between the lenses 24 and 30 is parallel. The first and second black point plates 26, 28 will be explained in detail hereinafter.

The photographing and observing optical system 40 is provided on a photographing axis 34 coincident with that of the light beam reflected by the apertured mirror 32. There are provided a first objective lens 36 and a second objective lens 35 on the axis 34 in front of the apertured mirror 32. On the axis 34 behind the apertured mirror 32 there are provided a diaphram plate 41 having an aperture 41a located just behind the mirror 32, an imaging lens 42, a swingable mirror 44 and a film 46 arranged in this order from the mirror 32. The photographing beam reflected at the retina $E_R$ reaches the film 46 through the lenses 35, 36, the apertures 32a, 41a and the imaging lens 42. A first space imaging point 48 of the retina $E_R$ is conjugate with the retina $E_R$ with respect to the lenses 35, 36, and the film 46 is located conjugate with the point 48 with respect to the lens 42. The pupil $E_p$ of an eye E is located so as to be conjugate with the apertured mirror 32 with respect to the lenses 35, 36.

There are further provided a field lens 52, a mirror 54 and an eyepiece 56 on an observing axis 50 reflected at the mirror 44. The field lens 52 is located close to a second space imaging point 60 which is conjugate with the first space imaging point 48 with respect to the lens 42, and the eyepiece 56 is located so as to focus at the second space imaging point 60.

In the optical system as mentioned above, the illuminating beam passing through the ring slit 20a forms a first image of the ring slit 20a on the apertured mirror 32, the beam thereby being reflected toward the objective lenses 35, 36 at the periphery of the mirror 32. Subsequently, the beam forms a second image of the ring slit 20a at the pupil $E_p$ through the lenses 35, 36, so that the beam passes through a peripheral portion of the pupil $E_p$ to illuminate the retina $E_R$.

The photographing beam reflected at the retina $E_R$ passes through a center portion of the pupil $E_p$ where the illuminating beam does not pass so as to form the first space image through the lens 35, 36 at the point 48. If the swingable mirror 44 is located so as to be horizontally directed as shown by a broken line in FIG. 1, the photographing beam reaches the film 46 through the apertures 32a, 41a, and the lens 42 to expose the film 46. If the mirror 44 is inserted into the photographing axis 34 as shown by a solid line in FIG. 1, the photographing beam is reflected at the mirror 44 and forms the second space image at the point 60, so that the beam is changed into a parallel beam through the eyepiece 56 to reach the eye 62 of the operator. The diaphragm plate 41 enhances the stop effect of the apertured mirror 32.

Preventing flares or ghosts from being generated by the lenses 35, 36 through which the illuminating and phtographing beams pass will now be described. The surfaces of the lenses 35, 36 are designated by $R_1$, $R_2$, $R_3$, $R_4$, respectively, in this order, from the eye E. It is assumed that a beam is passing through the aperture 41a and reflected at the surfaces $R_1$, $R_4$, $R_3$ to reach the black point plates 26, 28, respectively.

Figure 3:
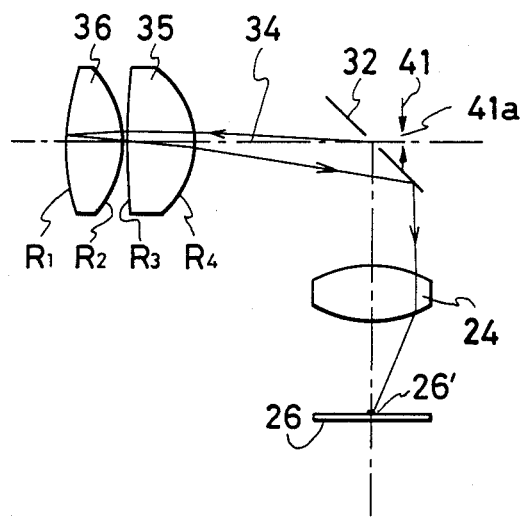
FIG. 3 through 6 are views for describing the prevention of flares or ghosts generated by light beams reflected at the surfaces $R_1$, $R_4$, $R_3$ and $R_2$, respectively.
Figure 4:
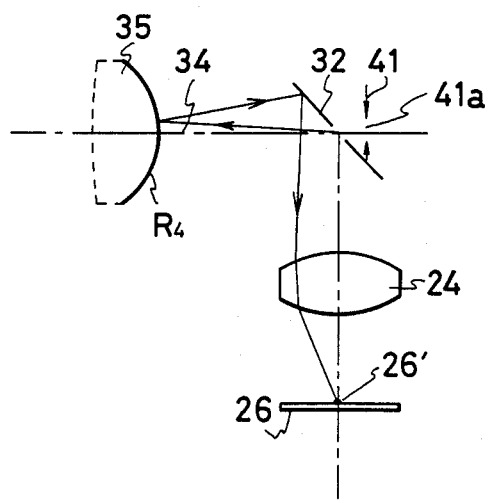

The beam reflected at the surface $R_1$, as shown in FIG. 3, will pass through the surfaces $R_2$, $R_3$, $R_4$ and be reflected at the apertured mirror 32 and pass through the lens 24 so as to form an image of the aperture 41a on the first black point plate 26. The beam reflected at the surface $R_4$, as shown in FIG. 4, is reflected at the apertured mirror 32 and passes through the lens 24 so as to form the image of the aperture 41a on the first black point plate 26. Namely, position and curvature radii of the surfaces $R_1$, $R_4$ are determined so that the beams reflected at the surfaces $R_1$, $R_4$ form the images of the aperture 41a on the first black point plate 26, and a diameter of the black point 26' is determined so that the black point 26' covers the images of the apertures 41a produced by the beams as mentioned above. As a result, the blcak point 26' blocks a part of the illuminating beam which have been reflected at the surfaces $R_1$, $R_4$ and been mixed with the photographing beam to form flares or ghosts.

Figure 5:
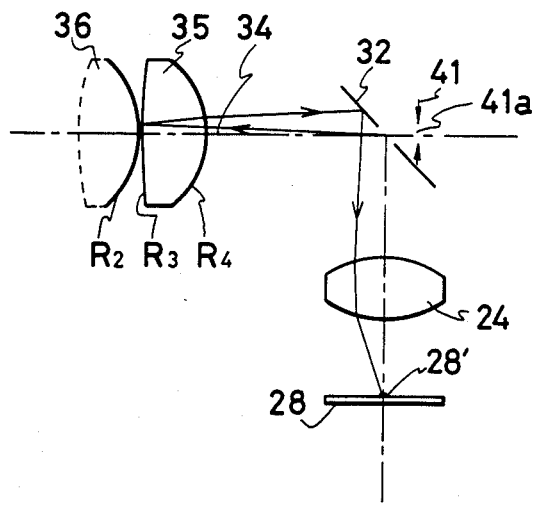

The beam reflected at the surface $R_2$, as shown in FIG. 5, passes through the surfaces $R_3$, $R_4$, is reflected at the apertured mirror 34 and through the lens 24 so as to form the image of the aperture 41a on the second black point plate 28. Namely, position and a curvature radius of the surface $R_2$ are determined so that the imaginary beam reflected at the surface $R_2$ forms the image of the aperture 41a on the second black point plate 28, and a diameter of the black point 28' is determined so that the black point 28' covers the image of the aperture 41a produced by the beam as mentioned above. As a result, the black point 28' blocks a part of the illuminating beam which have been reflected at the surface $R_2$ and have been mixed with the photographing beam to form flares or ghosts.

Figure 6:
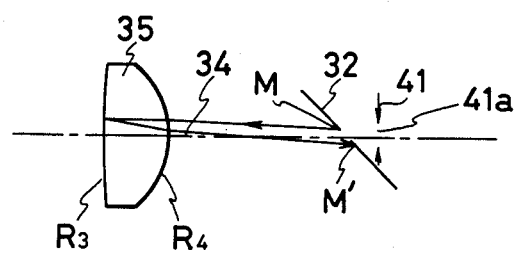
Figure 7:
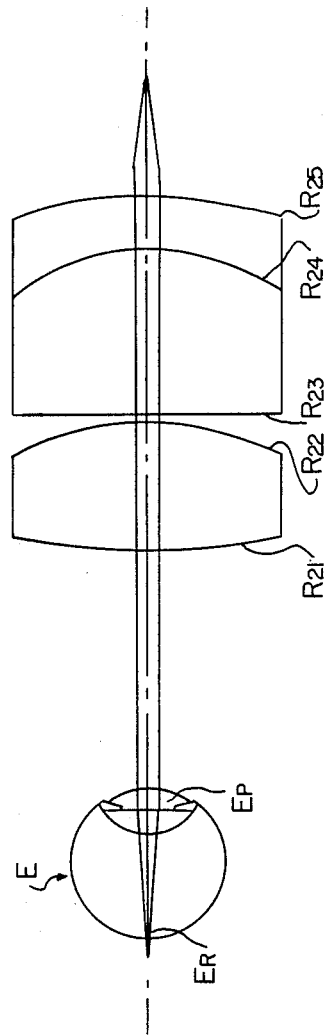

The beam reflected at a discretional point M of the apertured mirror 32, as shown in FIG. 6, passes through the surface $R_4$, is reflected at the surface $R_3$ and passes through the surface $R_4$ again so that the beam reaches a point M' of the mirror 32 which is symmetrical with the point M with respect to the axis 34. Namely, a position and a curvature radius of the surface $R_3$ is determined so that a center of the curvature of the surface $R_3$ is conjugate with the apertured mirror 32 with respect to the lens 35. Consequently, a part of the illuminating beam reflected at both the apertured mirror 32 and the surface $R_3$ cannot pass through the aperture 32a so that the beam reflected at the surface $R_3$ does not mix with the photographing beam and therefore does not generate flares or ghosts.

A first example of the design values of the objective lens according to the present invention is as follows (unit:mm):

| Surface | Curvature radius | Spacing or thickness | Refractive index | Abbe number |
|---|---|---|---|---|
| $R_{11}$ | $r_1 = 80.0$ | $d_1 = 23.0$ | $Nd = 1.58913$ | $\nu = 61.0$ |
| $R_{12}$ | $r_2 = -44.45$ | $d_2 = 1.0$ | $Nd = 1.0$ | |
| $R_{13}$ | $r_3 = 3000.0$ | $d_3 = 33.0$ | $Nd = 1.51633$ | $\nu = 64.1$ |
| $R_{14}$ | $r_4 = -60.7$ | | | |

Angle of view 60°
magnification of pupil = 2.1×
working distance 43.0

The surfaces $R_{11}$, $R_{12}$, $R_{13}$, $R_{14}$ correspond respectively to the surfaces $R_1$, $R_2$, $R_3$, $R_4$ mentioned above. Since the surfaces $R_{12}$, $R_{14}$ are of nonspherical configurations, the values relative thereto show the curvature radii of their basic spherical surfaces. When the pupil $E_p$ and the aperture 32a are conjugate to each other with respect to the objective lens, the nonspherical surfaces $R_{12}$, $R_{14}$ are designed so that spherical aberration is corrected appropriately.

A second example of the design values of the objective lens according to the present invention is as follows (unit:mm):

| Surface | Curvature radius | Spacing or thickness | Refractive index | Abbe number |
|---|---|---|---|---|
| $R_{21}$ | $r_1 = 80.0$ | $d_1 = 23.0$ | $Nd = 1.58913$ | $\nu = 61.0$ |
| $R_{22}$ | $r_2 = -44.45$ | $d_2 = 1.0$ | $Nd = 1.0$ | |
| $R_{23}$ | $r_3 = 3000.0$ | $d_3 = 25.0$ | $Nd = 1.58913$ | $\nu = 61.0$ |
| $R_{24}$ | $r_4 = -42.6$ | $d_4 = 10.3$ | $Nd = 1.78472$ | $\nu = 25.7$ |
| $R_{25}$ | $r_5 = -61.26$ | | | | angle of view 60°
magnification of pupil = 2.1×
working distance 43.0

The surfaces $R_{21}$, $R_{22}$, $R_{23}$, $R_{25}$ correspond respectively to the surfaces $R_1$, $R_2$, $R_3$, $R_4$ mentioned above. Position and curvature radius of the surface $R_{25}$ were designed so that the beam projected from the aperture 41a and reflected at the surface $R_{25}$ forms an image of the aperture 41a on the first black point 26'.

It is not necessary that the beam reflected at the surfaces $R_1$, $R_4$ form the images of the aperture 41a on the first black point 26' precisely and the images of the apertures 41a made by the beams have the same size as each other, but the first black point 26' should be designed so that it blocks completely the area where the imaginary beam passes on the first black point plate 26. The second block point 26' may be designed in the same way as the first block point 26' as mentioned above.

I claim:

1. An optical system for a retinal camera comprising:
   objective lens means adapted to be placed opposite to a patient's eye with an air space therebetween having a first biconvex type lens means with a first surface and second surface, and a second biconvex type lens means with a third surface and fourth surface, wherein when said objective lens means is placed opposite to a patient's eye said first biconvex type lens means is located between the eye and said second biconvex type lens means, and said first surface faces towards the patient's eye while said second surface faces away from the eye, said third surface faces toward said second surface while said fourth surfaces faces opposite said third surface, the radius of curvature of said first surface being greater than the radius of curvature of said second and fourth surfaces, the radius of curvature of said fourth surface being greater than that of said second surface but less than that of said first surface, the radius of curvature of said third surface being greater than that of said first, second and fourth surfaces,
   an illumination optical system for projecting beams of illumination light through said objective lens means to said patient's eye, said illumination optical system including beam restriction means for passing selected beams of said illumination light to said objective lens means,
   a photographing optical system for observing the retina of said patient's eye through said objective lens means,
   optical path dividing means being provided on the opposite side of the objective lens means from that of the eye for dividing the optical path passing through the objective lens means into two sub-optical paths, said photographing optical system being located on one of the sub-optical paths, said illuminating optical system being located on the other sub optical path, said illuminating optical system further comprising harmful beam blocking means disposed so as to block images of the beam restriction means produced by light reflected at said convex surfaces of said first and second biconvex lens means, whereby said images are not introduced into said photographing optical system.

2. An optical system in accordance with claim 1 in which the second and fourth convex surfaces are of nonspherical configurations.

3. An optical system in accordance with claim 2 in which the center of curvature of the third convex surface is conjugate with the beam restriction means with respect to the second biconvex type lens means.

4. An optical system in accordance with claim 2 in which the second biconvex type lens means consists of a biconvex lens and a meniscus lens which are joined to each other.

5. An optical system in accordance with claim 4 in which the photographing optical system has a beam restriction means, and the first and fourth convex surfaces and the joined surface of the second biconvex type lens means are designed so that images of the beam restriction means reflected at these surfaces are formed at the same position where the harmful beam blocking means is provided.

6. An optical system in accordance with claim 5 in which the center of the curvature of the third convex surface is conjugate with the beam restriction means with respect to the second biconvex type lens means.

* * * * *

UNITED STATES PATENT AND TRADEMARK OFFICE
CERTIFICATE OF CORRECTION

PATENT NO. : 4,838,680
DATED : June 13, 1989
INVENTOR(S) : Kazuo Nunokawa

It is certified that error appears in the above-identified patent and that said Letters Patent is hereby corrected as shown below:

First page, following Item [22], insert:

--RELATED U.S. APPLICATION DATA
[63] Continuation of Ser. No. 736,560, May 21, 1985, abandoned--;

Column 1, line 40, "aberations" should read -- aberrations--;

Column 5, line 61, "26'" should read "28'".

Signed and Sealed this

Ninth Day of October, 1990

Attest:

HARRY F. MANBECK, JR.

Attesting Officer

Commissioner of Patents and Trademarks